United States Patent
Marshall et al.

[11] Patent Number: 6,136,013
[45] Date of Patent: Oct. 24, 2000

[54] LANCET DEVICE

[75] Inventors: Jeremy Marshall; David Danvers Crossman; Ernest John Mumford, all of Oxford, United Kingdom

[73] Assignee: Owen Mumford Limited, Oxford, United Kingdom

[21] Appl. No.: 09/269,027

[22] PCT Filed: Sep. 17, 1997

[86] PCT No.: PCT/GB97/02480

§ 371 Date: Mar. 18, 1999

§ 102(e) Date: Mar. 18, 1999

[87] PCT Pub. No.: WO98/11821

PCT Pub. Date: Mar. 26, 1998

[30] Foreign Application Priority Data

Sep. 18, 1996 [GB] United Kingdom .................. 9619462

[51] Int. Cl.[7] .................................................. A61B 17/32
[52] U.S. Cl. ........................... 606/167; 606/181; 606/182
[58] Field of Search .................................... 606/167, 181, 606/182, 183, 184, 185; 600/578, 576

[56] References Cited

U.S. PATENT DOCUMENTS

| | | | |
|---|---|---|---|
| 3,760,806 | 9/1973 | Camppbell, Jr. ........................ | 128/314 |
| 4,983,178 | 1/1991 | Schnell . | |
| 5,196,025 | 3/1993 | Ranalletta et al. ...................... | 606/182 |
| 5,397,334 | 3/1995 | Schenk et al. .......................... | 606/182 |

FOREIGN PATENT DOCUMENTS

| | | |
|---|---|---|
| 0 433 050 | 6/1991 | European Pat. Off. . |
| 0 714 631 | 6/1996 | European Pat. Off. . |
| WO 93/19671 | 10/1993 | WIPO . |

*Primary Examiner*—Michael Buiz
*Assistant Examiner*—Lien Ngo
*Attorney, Agent, or Firm*—Young & Thompson

[57] ABSTRACT

A lancet device has a two part housing (1) integrally molded in a folded-out configuration with a spring (2), a lancet body (3) encasing a needle (4), and a needle cap (5) concealing the needle tip. The spring (2) is a zig-zag connected at one end to one housing part (7) by a web (19) and merging at the other end into the lancet body (3). This is folded over with the spring (2) about the web (19) into the housing part (7), and the other housing part (6) is closer over about web hinges (8) and fastened. A trigger (9) is incorporated in the other housing part (6) and is deformable inwardly to release the lancet body (3) from a catch arrangement (14, 21) which holds the lancet retracted with the spring energized. The needle cap (5) can be used for the retraction before being removed.

7 Claims, 2 Drawing Sheets

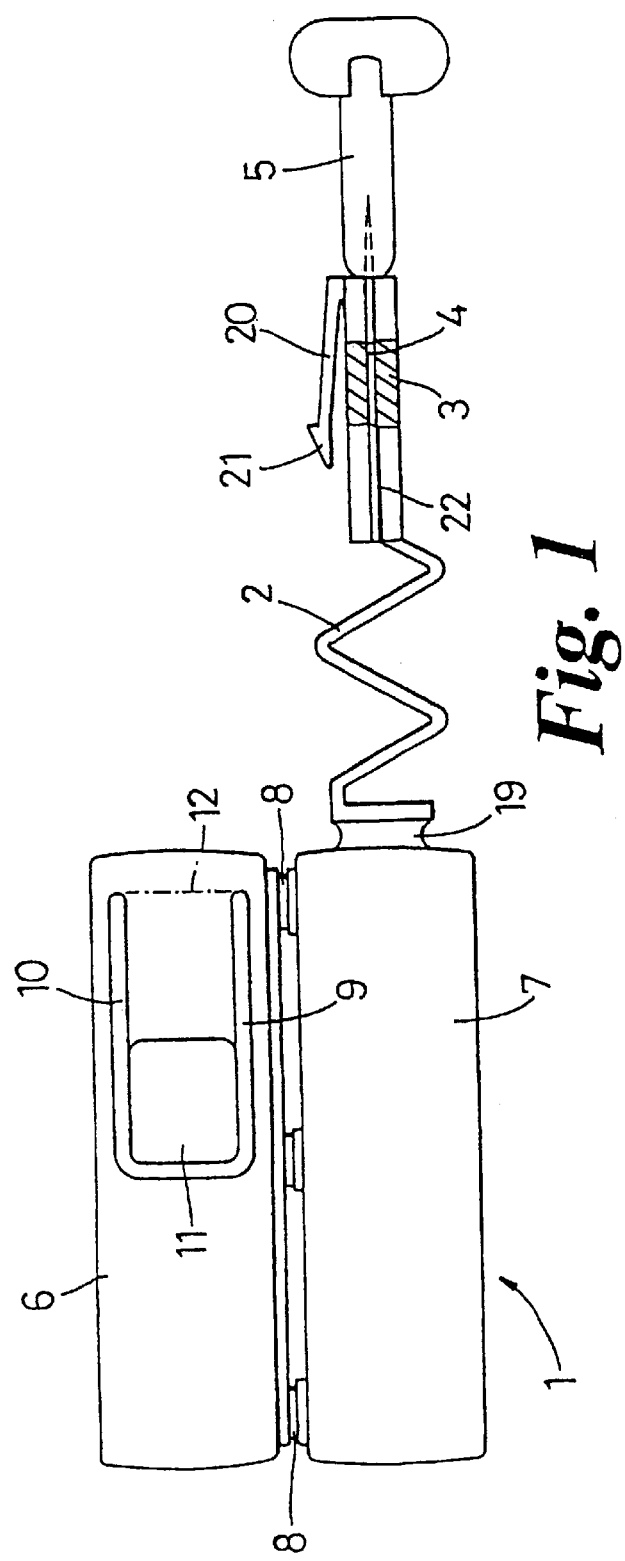
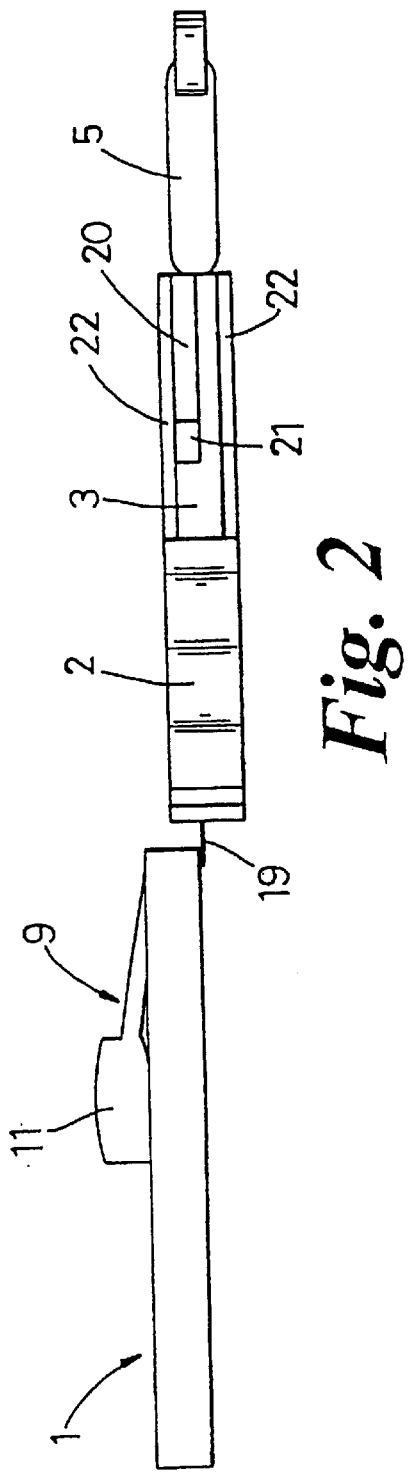

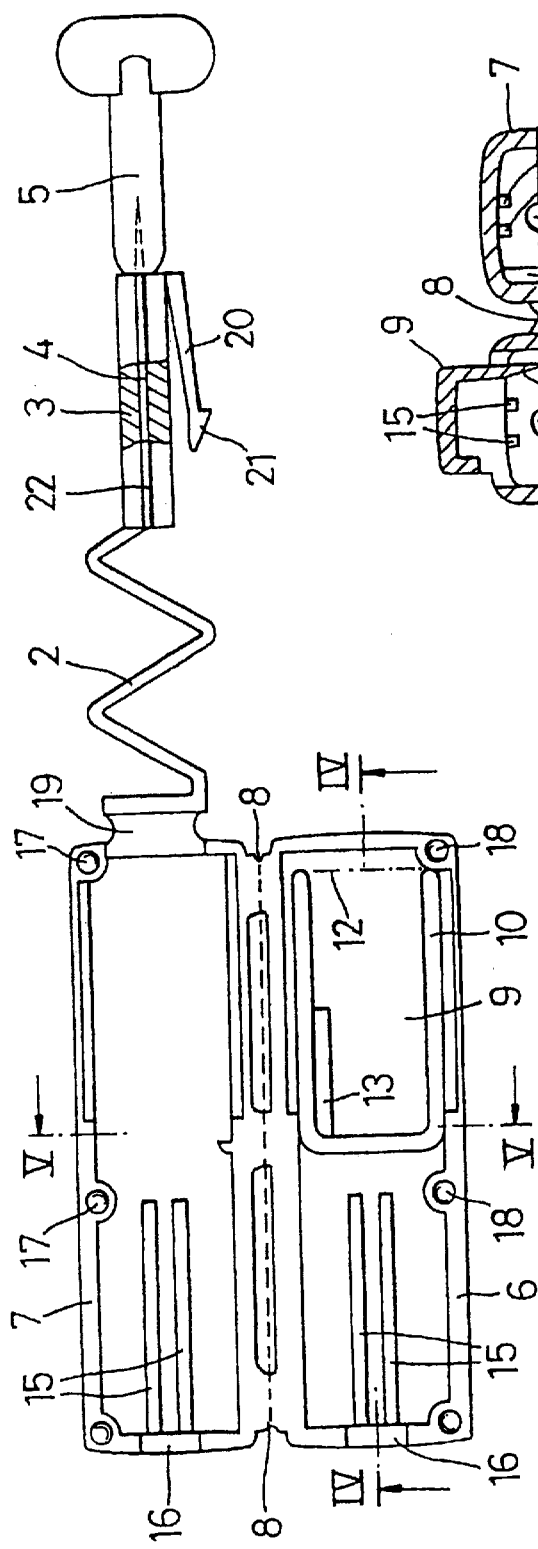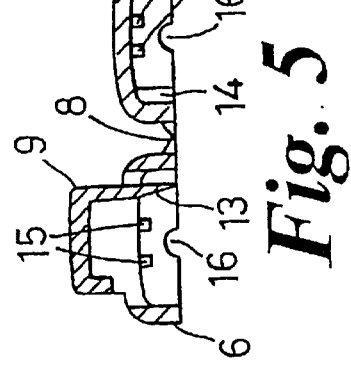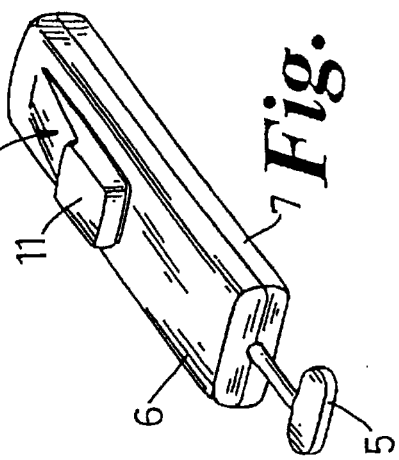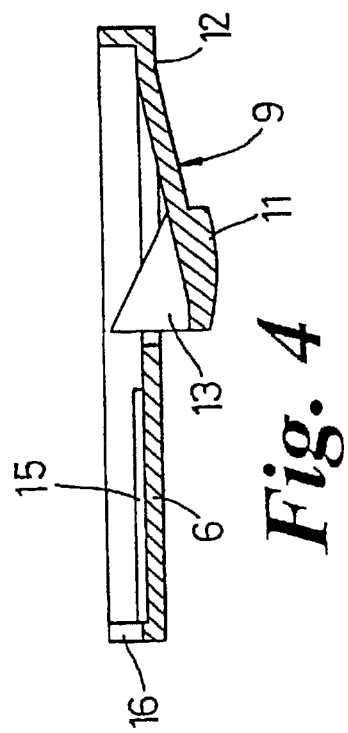

LANCET DEVICE

FIELD OF THE INVENTION

This invention relates to lancet devices. They are used for pricking the skin to take blood samples.

BACKGROUND OF THE INVENTION

There are two main kinds. One has a reusable firing mechanism in which a disposable lancet is loaded, and after use the lancet has to be unloaded and safely disposed of. The other kind has the lancet as part of a trigger device, the whole of which is thrown away after a single use. These are small and simple, to be economic, but nevertheless they have hitherto generally required several parts, separately moulded or otherwise fabricated, to be assembled together. The less the number of parts and the fewer the assembly operations the better for such throwaway items.

OBJECT OF THE INVENTION

It is the aim of this invention to reduce this kind of lancet device to the minimum number of parts.

SUMMARY OF THE INVENTION

According to the present invention there is provided a lancet device in which a multi-part housing, trigger, spring and lancet body are integrally moulded from plastics material in a folded-out configuration, components of the moulding being joined by webs which enable the housing parts, one of which incorporates the trigger, to be hinged and fastened together with the spring and lancet within the housing.

The housing parts are conveniently two elongate channel members joined by a web or webs between longitudinal edges. They then hinge closed when the lancet and spring are folded over into one of the channels.

The spring may be a zig-zag formation, joined at one end by a web hinge to the rear end of a housing part (preferably the one without the trigger) and merging into the lancet body at the other end. Conveniently, the trigger is a tongue deformable inwardly to co-operate with and disengage catch means holding the lancet retracted. The catch means may be a toothed finger and a detent, one of these being on the side of the lancet body and the other inside a housing part, the toothed finger having snap engagement with the detent on completion of lancet retraction. Preferably, the lancet carries the finger while the detent is on the housing.

The lancet body will be moulded around a needle whose tip projects from the forward end of the lancet body. Preferably, a tear-off cap, initially concealing the needle tip, is integrally moulded with the lancet body, part of the cap being accessible outside the forward end of the housing when that is closed around the lancet body and spring. The cap may be elongated and usable, before being removed from the needle tip, to push the lancet body back to temporary retention by catch means releasable by the trigger. This primes the device in the manner of EP-B-0634000.

BRIEF DESCRIPTION OF THE DRAWINGS

For a better understanding of the invention, one embodiment will now be described, by way of example, with reference to the accompanying drawing, in which:

FIG. 1 is a plan view of a lancet device as moulded and before completion, showing the outside of the housing, FIG. 2 is a side view of the lancet device in that condition, FIG. 3 is a plan view, similar to FIG. 1, but showing the inside of the housing, FIG. 4 is a section on the line IV—IV of FIG. 3, FIG. 5 is a section in the line V—V of FIG. 3, and FIG. 6 is a perspective view of the completed lancet device.

DETAILED DESCRIPTION OF THE INVENTION

The device has a two-part housing 1, a spring 2, a lancet body 3 containing a needle 4, and a needle cap 5 concealing the tip of the needle 4 which projects from the body 3. These components 1, 2, 3 and 5 are integrally moulded, embedding the needle 4.

The housing 1 is in two elongate parts 6 and 7, both generally channel shaped and connected at adjacent longitudinal edges by thin flexible webs 8 which form hinges enabling the parts to be closed together. The part 6 has a trigger 9 in the form of a tongue provided by a U-shaped cut out 10 open in the rearward direction. The plastics material will allow this tongue, when pressed by a pad 11 at its free end, to flex about the transverse line 12. On the inside, one side of the pad 11 is formed with a blade 13 which will project into the housing when the parts 6 and 7 are closed together.

The other part 7 has a tooth 14 projecting inwards laterally from the hinged side, about half way along its length.

Both parts 6 and 7 have central pairs of guide ribs 15 extending from the forward end to near the half length point, and at this forward end the transverse flanges have central semi-circular recesses 16 which will combine to provide an aperture for the stem of the cap 5. Along their free longitudinal edges the part 7 has studs 17 while the part 6 has corresponding sockets 18 into which the studs 17 will snap when the housing 1 is closed together.

One end of the zig-zag spring 2 is connected to the rear end of the part 7 by a thin web 19 which forms a hinge, and its other end merges into the lancet body 3. This has a finger 20 extending rearwardly and slightly outwardly from its forward end and terminating in a wedged hook 21. The plastics material makes this finger 20 resiliently flexible. The lancet body 3 also has longitudinal ribs 22 extending along opposite sides.

While the preferred arrangement is shown, it may be possible to swap the tooth 14 and the finger 20, having the tooth on the lancet body and the finger on a housing part.

To complete the device, the spring 2 and the lancet 3 with its cap 5 are folded over through 180° about the web hinge 19 so that the spring lies within the rearward part of the body 7 and one of the lancet body ribs 22 fits between the ribs 15 of that part. The stem of the cap 5 is cradled by the recess 16. Then the part 6 is folded over about the web hinges 8 to snap fit to the part 7, enclosing the spring 2 and the lancet 3 and bringing its pair of ribs 15 into co-operation with the other lancet body rib 22. The closure may be made even more secure by adhesive or welding. The cap 5 projects through the aperture formed by the recesses 16.

To prime the device, the cap 5 is pressed in, and the wedged hook 21 snaps past the tooth 14 and engages behind it. The lancet is thus held retracted.

For use, the cap 5 is twisted off (the lancet body 3 will not rotate since it is held against that by the interengaging ribs 15 and 22), the forward end of the device is applied to the skin and the pad 11 is pressed. The blade 13 engages the outer side of the hook 21, and flexes that in towards the body 3, thereby disengaging the hook from the tooth 14. The spring 2 then acts to fire the lancet forwards and the needle tip briefly projects before retracting safely behind the recesses 16.

What is claimed is:

1. A lancet device comprising a housing with a first part and a second part, a spring, a lancet body extending from one end of the spring, a first web joining the first and second parts of the housing so that, as molded, those parts are in a folded-out configuration but which enables said parts to be hinged together, a second web joining the other end of the spring to the first housing part so that, as molded, the spring and lancet body are folded out from said first housing part but which enables the spring and lancet body to be hinged over said first housing part and to be captive within the housing when the two parts are hinged and fastened together, and a trigger on one of the housing parts arranged to retain the lancet body within the housing with the spring compressed when the housing parts are hinged and fastened together, but which is actuable to release the lancet body to cause the exposed tip of a needed embedded therein momentarily to project through an aperture in the housing, the housing parts, the webs, the spring, the lancet body and the trigger all being integrally molded from plastics material.

2. A lancet device as claimed in claim 1, wherein the housing parts are two elongate channel members and the first web is between longitudinal edges.

3. A lancet device as claimed in claim 2, wherein the spring is a zig-zag formation and the second web joins it to an end of the first part of the housing.

4. A lancet device as claimed in claim 1, wherein a tear-off cap, initially concealing the needle tip, is integrally molded with the lancet body, part of the cap being accessible outside the housing when that is closed around the lancet body and compressed spring.

5. A lancet device as claimed in claim 1, wherein the trigger is a tongue deformable inwardly of the housing to co-operate with and disengage catch means holding the lancet body retracted.

6. A lancet device as claimed in claim 5, wherein the catch means is a toothed finger and a detent, one of these being on the side of the lancet body and the other inside a housing part, the toothed finger having snap engagement with the detent on completion of lancet retraction.

7. A lancet device as claimed in claim 4, wherein the cap is elongated and is usable, before being removed from the needle tip, to push the lancet body back to temporary retention by catch means releasable by the trigger.

* * * * *